(12) United States Patent
Gunnarsson et al.

(10) Patent No.: US 9,248,032 B2
(45) Date of Patent: Feb. 2, 2016

(54) SUSPENSION LINER SYSTEM WITH DISTENSIBLE SEAL

(75) Inventors: Bjarni Gunnarsson, Reykjavik (IS); Olafur Halldorsson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 262 days.

(21) Appl. No.: 13/271,692

(22) Filed: Oct. 12, 2011

(65) Prior Publication Data
US 2012/0095571 A1    Apr. 19, 2012

Related U.S. Application Data

(60) Provisional application No. 61/393,015, filed on Oct. 14, 2010.

(51) Int. Cl.
*A61F 2/78* (2006.01)
*A61F 2/30* (2006.01)

(52) U.S. Cl.
CPC ............. *A61F 2/7812* (2013.01); *A61F 2/7843* (2013.01); *A61F 2002/30136* (2013.01)

(58) Field of Classification Search
CPC . A61F 2/80; A61F 2/7812; A61F 2002/7818; A61F 2/7843
USPC .......................................................... 623/36
See application file for complete search history.

(56) References Cited

U.S. PATENT DOCUMENTS

| | | | |
|---|---|---|---|
| 1,057,562 A | 4/1913 | La Point | |
| 4,128,903 A | 12/1978 | Marsh et al. | |
| 4,923,474 A | 5/1990 | Klasson et al. | |
| 4,923,475 A * | 5/1990 | Gosthnian et al. | 623/37 |
| 5,108,456 A | 4/1992 | Coonan, III | |
| 5,156,629 A | 10/1992 | Shane et al. | |
| 5,314,497 A * | 5/1994 | Fay et al. | 623/34 |
| 5,387,245 A | 2/1995 | Fay et al. | |
| 5,507,836 A * | 4/1996 | Pohlig | 623/37 |
| 5,724,714 A | 3/1998 | Love | |
| 5,830,237 A * | 11/1998 | Kania | 623/37 |
| 5,888,230 A * | 3/1999 | Helmy | 623/34 |
| 5,980,577 A * | 11/1999 | Radis et al. | 623/36 |
| 6,136,039 A | 10/2000 | Kristinsson et al. | |
| 6,231,617 B1 * | 5/2001 | Fay | 623/36 |
| 6,485,776 B2 | 11/2002 | Janusson et al. | |
| 6,706,364 B2 | 3/2004 | Janusson et al. | |
| 6,923,834 B2 | 8/2005 | Karason | |

(Continued)

FOREIGN PATENT DOCUMENTS

KR   10-2009-0019051 A   2/2009
WO        2008/030346 A2   3/2008

OTHER PUBLICATIONS

International Search Report and Written Opinion issued in related international application PCT/2011/056093, Jan. 1, 2012, 10 pages.

*Primary Examiner* — Bruce E Snow
*Assistant Examiner* — Melissa Hoban
(74) *Attorney, Agent, or Firm* — Workman Nydegger

(57) ABSTRACT

A suspension liner is adapted to provide an interface between a residual limb and a prosthetic socket. The liner includes an elongate, generally conical body portion, and a volume control pad located along the body portion. The volume control pad is arranged to distend outwardly from the body portion. A resilient seal element is connected to the body portion and protrudes radially from the body portion, and is located in correspondence with the volume control pad.

14 Claims, 3 Drawing Sheets

(56) References Cited

U.S. PATENT DOCUMENTS

| | | |
|---|---|---|
| 6,936,073 B2 | 8/2005 | Karason |
| 6,964,688 B1 | 11/2005 | Kania |
| 7,118,602 B2 | 10/2006 | Bjarnason |
| 7,169,189 B2 | 1/2007 | Bjarnason et al. |
| 7,655,049 B2 | 2/2010 | Phillips |
| 8,034,120 B2 | 10/2011 | Egilsson et al. |
| 2007/0225824 A1* | 9/2007 | Einarsson ............ 623/36 |

* cited by examiner

SUSPENSION LINER SYSTEM WITH DISTENSIBLE SEAL

CROSS-REFERENCE TO RELATED APPLICATION

This application claims the benefit of priority from U.S. provisional application No. 61/393,015, filed on Oct. 14, 2010. The entirety of the provisional application is incorporated herein by reference.

BACKGROUND a. Field of the Invention

This invention relates to suspension liners adapted to provide an interface between a residual limb and a prosthetic socket.

b. Discussion of Related Art

The use of suspension liners adapted to provide a soft, flexible interface between a residual limb of an amputee and a hard socket to which a prosthetic device is secured is known in the art generally, as exemplified by U.S. Pat. No. 4,923,474. Such suspension liners are typically made of an air impermeable elastomer material such as silicone and may include a reinforcement layer intermediate the inner and outer surfaces of the suspension liner body portion or externally thereof to provide resistance against axial elongation of the elastomer constituting the suspension liner body. Such reinforcement typically does not restrict radial distension or stretching of the suspension liner body.

In accordance with prior art teachings, these suspension liners may function to secure the residual limb within the prosthetic socket member once the residual limb and sleeve are inserted into the socket in a close-fitting relationship by isolating the distal end area of the hard socket from the atmosphere. Upon application of a pulling force on the suspension liner relative to the socket, suction is created in the distal end of the socket tending to retain the suspension liner within the socket. Appropriate devices are usually provided to enable expulsion of air between the distal end of the suspension liner and the hard socket, and to isolate the distal end of the hard socket member from the atmosphere after the suspension liner with a residual limb has been fully inserted within the socket member.

In some applications, the suspension liner is provided with an umbrella at its distal end and a threaded socket for receiving a prosthetic securing pin member which then extends through an axial opening in the distal end of the hard socket member for securing the socket member relative to a prosthetic device mounted to the distal end of the socket member.

In other applications, the prosthetic device is secured to the exterior of the distal end of the hard socket member and the sleeve member is fully contained within the hard socket member.

The elastomer constituting the suspension liner member frictionally engages and remains attached to the skin of a residual limb so that the limb is retained within the hard socket member in a comfortable, non-irritating manner. The suspension liner may be thickened to provide cushioning effect between the residual limb and the hard socket, which is typically custom made to closely fit the residual limb. Suspension liners of this kind are used for both trans-tibial (TT) amputees as well as trans-femoral (TF) amputees. That is, the suspension liners may be utilized for applications above the knee or below the knee of the amputee.

In other applications, it may be desired to more positively secure the suspension liner within the socket by creating a hypobaric (vacuum) pressure within the distal end of the hard socket between such distal end and the distal end of a suspension liner inserted into the socket with a residual limb contained within the suspension liner. The hypobaric pressure may be maintained at the distal end of the hard socket and the interior of the socket at its distal end will be isolated from atmosphere during normal retention of the sleeve liner within the socket. Opening the distal end of the socket to atmosphere releases the vacuum or hypobaric pressure within the socket to enable simple withdrawal of a residual limb with a suspension liner thereon from the socket.

A pump or other device may be utilized to evacuate the distal end of the socket between the distal end of a suspension liner and the distal end of a socket. A valve or other appropriate device typically is used to open and close the distal end of a socket to surrounding atmosphere.

Various arrangements are known in the prior art for providing an appropriate seal between the exterior of the suspension liner and the interior of the hard socket including external air impermeable sleeves covering the interface area between the proximal end of the hard socket and the adjacent suspension liner body.

In trans-femoral applications, the sealing between a suspension liner and a socket is generally simpler and easier to execute than sealing a trans-tibial suspension liner against the inner surface of a socket because in the latter situation, the residual limb contains more bony protuberances and irregular shapes that are difficult to effectively seal, particularly if it is desired to simply use the material of the elastomeric suspension liner as the sealing element.

While many of these known suspension sleeves having seal have been effective, it has been found that there are variations in the hard sockets including open spaces that minimize the effectiveness of the seal elements. Moreover, the residual limbs have a tendency to undergo volume fluctuations that may impair the success of the sealing interface between the seal element and the hard socket.

SUMMARY

This disclosure pertains to a suspension liner adapted to provide an interface between a residual limb and a prosthetic socket, and securely retain the residual limb with the prosthetic socket.

An embodiment of the suspension liner includes an elongate, generally conical body portion formed from at least one material segment that is at least radially elastically extensible from a relaxed non-extended condition and includes proximal and distal end areas. The liner may have at least one resilient seal element protruding radially from the liner body portion, and extend about and from at least a portion of the periphery of the liner body portion. A volume control pad preferably is located between the body portion and the seal element, and is arranged to distend from the body portion and urge the seal element outwardly relative to and from the body portion.

The seal element may annularly extend about the body portion, and the volume control pad annularly extends between the body portion and the seal element. The volume control pad may be arranged in correspondence to the seal element, or offset relative to the seal element such that the volume control pad and the seal element at least overlap in part.

The volume control pad is preferably selectively adjustable in size and pressurized, to thereby allow for control of the volume of the pad and regulate the extension of the seal element relative to the body portion. In accordance with achieving the selective size and pressurization of the volume control pad, a passageway may be defined within the thickness of the body portion and in correspondence with the volume control pad to allow for fluid communication with a source and the volume control pad. Of course, the volume control pad may be pressurized by other know means, and the passageway is not limited to being formed within the thickness of the liner body.

A continuous textile material may cover portions of the body portion above and below, or adjacent to end portions of the seal element. The body portion may be formed at least in part from an elastomeric polymer, whereas the seal element may be formed from an outer seal piece fixedly secured to the peripheral circumference of the body portion. The outer seal piece may likewise be formed from an elastomeric material.

The liner may be provided with or without the seal element, wherein in the instance that the liner lacks the seal element, pressurization of the volume control pad may be sufficient to securely retain the liner against a rigid socket and form a frictional fit. The volume control pad may be secured against the body portion by an adhesive, fastener or similar substance or element to firmly retain it against the body portion, or alternatively an outer layer may cover the volume control pad such that the volume control pad is located between the outer layer and the body portion.

The numerous advantages, features and functions of the various embodiments of the suspension liner will become readily apparent and better understood in view of the following description and accompanying drawings. The following description is not intended to limit the scope of the suspension liner, but instead merely provides exemplary embodiments for ease of understanding.

BRIEF DESCRIPTION OF THE DRAWINGS

The inventive suspension liner is described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein. The drawing figures are not necessarily drawn to scale, but instead are drawn to provide a better understanding of the components thereof, and are not intended to be limiting in scope, but rather to provide exemplary illustrations.

DETAILED DESCRIPTION OF VARIOUS EMBODIMENTS

A. Overview

Figures 1, 2, 3:
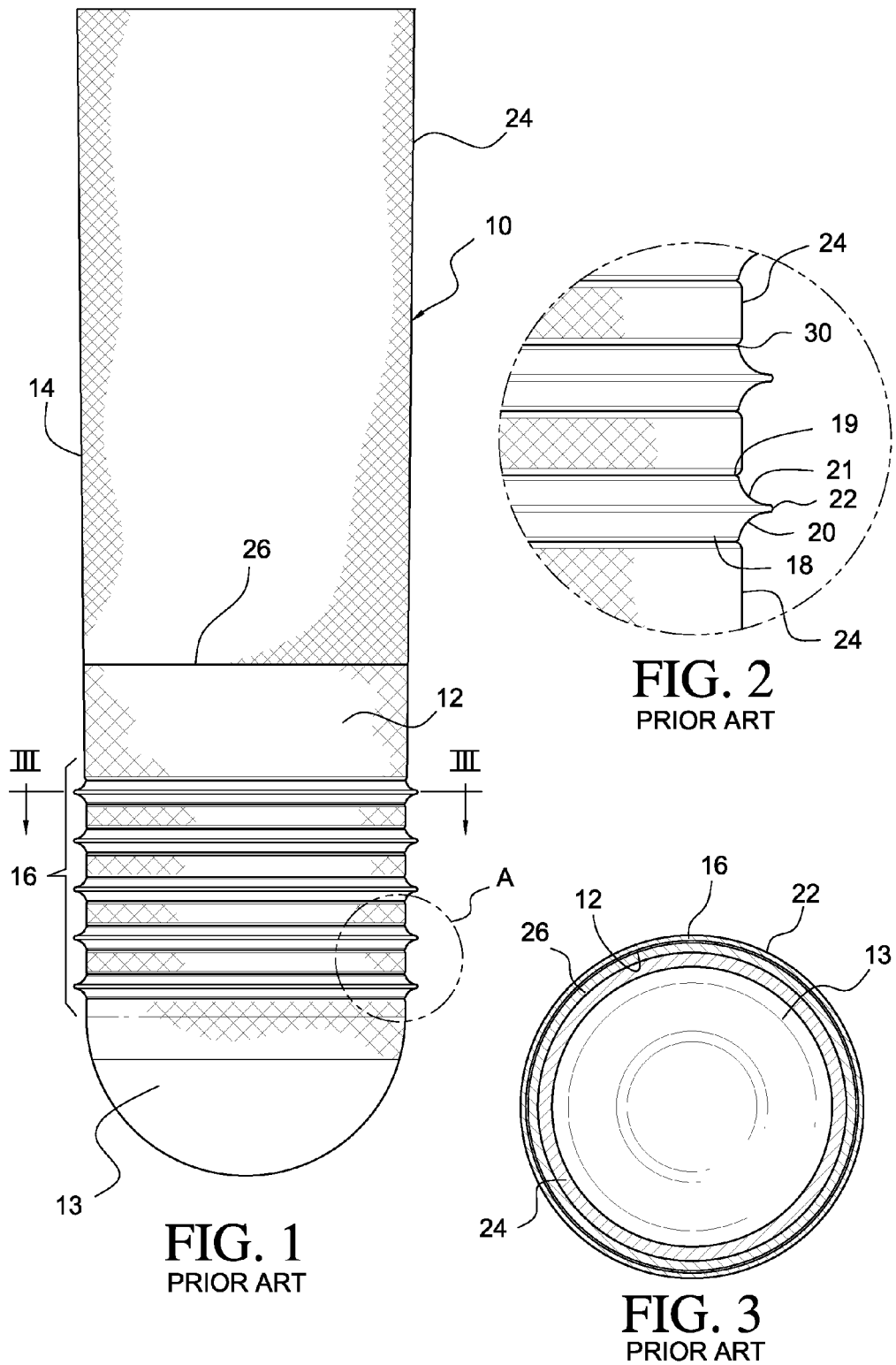
FIG. 1 shows an elevational view of a prior art suspension liner with a seal.
FIG. 2 is a detail view corresponding to detail A in FIG. 1.
FIG. 3 is a cross-sectional view taken along line II-II in FIG. 1.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

The anatomical terms described herein are not intended to detract from the normal understanding of such terms as readily understood by one of ordinary skill in the art of prosthetics. For example, the term "distal" is used to denote the portion or end of a limb or device that is farthest from the central portion of the body. The term distal is the opposite of "proximal" which is used to denote that the end or portion of the limb or device is nearer to the central portion of the body.

Some of the components described herein share similarities to components in U.S. Pat. No. 8,034,120, incorporated herein by reference and belonging to the assignee of this disclosure.

B. Embodiments of the Suspension Liner with a Distendable Seal

FIGS. 1-3 show an exemplary prior art suspension liner embodiment having a seal element and taken from U.S. Pat. No. 8,034,120. This liner 10 includes an elongate, generally conical body portion formed from first and second material segments 12, 14 and is at least radially elastically extensible from a relaxed non-extended condition and including proximal and distal end areas. The first and second material segments 12, 14 are secured to one another along a seam 26. The liner 10 defines a continuous profile 24 extending between the distal and proximal end areas, and a distal reinforcing cup or umbrella 13 may be provided at the distal end of the liner 10. The first and second material segments 12, 14 may both define the outer surface of the liner 10.

The liner 10 includes a plurality of resilient seal elements 16 protruding radially from the first material segment 12 and beyond the liner profile 24. The plurality of seal elements 16 may extend either partially or entirely around an outer peripheral portion of the first material segment 12.

Each of the seal elements 16 includes a distal root 18 extending from the liner profile 20. A distal arcuate section 20 projects from the distal root 18 and terminates at a peak 22. A proximal arcuate section 21 extends from the peak 22 to a proximal root 19. The seal elements 16 are arranged for deflection towards the liner profile 24 of the liner 10 when donned on a residual limb and placed within a prosthetic socket.

A recess 30 is generally formed at both the distal and proximal roots 18, 19. The recess 30 decreases friction at the roots 18, 19, against a hard, definitive socket when the liner 10 is worn in combination with the hard socket. The recess 30 provides a peel-off effect when the liner is removed from the socket, wherein the recesses may allow for a pistoning effect to break the seal of the liner against the socket.

It follows that the recess eliminates or minimizes shear forces existent between the socket and the liner, especially removal. Through these attributes of the recesses, the recesses improve the durability of the seal elements and thus the liner by reducing wear on the seals themselves by decreasing pressure points at the seal roots.

Of course, it will be noted that the liner according to the invention is not limited to the seal element according to U.S. Pat. No. 8,034,120, but may have any type of seal element known in the art. Alternatively, the liner according to the invention is not limited to having a seal element, but certain embodiments described herein may be provided without a seal element.

FIG. 3 specifically exemplifies the construction of the liner 10 along the first material segment 12. The liner 10 may have a dual polymeric or silicone layer construction, such as different silicone layers 24, 26, as taught in U.S. Pat. No. 6,136,039, owned by the assignee of this disclosure and incorporated herein by reference. The silicone layers 24, 26, each have a different hardness, wherein the outer layer 26 is harder than the inner layer 24. The first material segment 12 is generally adhered to the outer layer 26. At areas of the seals 16, a portion of the silicone of the outer layer 26 extends through the first material segment 12.

The exemplary liner 10 may be constructed in accordance with the following method. First and second material segments, preferably formed from a textile material, are sewn together along a common seam. The distal reinforcing cup is then molded onto the first material segment. The sewn together first and second material segments are placed into a liner mold, much in a same manner and using similar matrix materials as taught in U.S. Pat. No. 6,485,776, commonly owned by the assignee of this disclosure and incorporated herein by reference. Unlike U.S. Pat. No. 6,485,776, however, the liner mold includes a plurality of small annular grooves corresponding to the seal elements 16.

As in U.S. Pat. No. 6,136,039, two types of an elastomeric material such as silicone are injected into the mold, with the first silicone having a higher hardness when cured than the second silicone. Because the grooves in the molds are relatively small, and the pressure in the mold is relatively high, the first silicone is squeezed through first material segment into the grooves of the mold. It will be noted that whereas the first material segment is generally stiffer in nature than the second material segment, the first material segment is selected on the basis that it does not stretch into the grooves of the mold, thereby allowing only the first silicone to pass through the first material segment to form the plurality of seals.

The liner of any of the following embodiments herein may be constructed in the manner described above in reference to the embodiment of FIGS. 1-3. Moreover, the liner is not limited to having two layers of silicone each with a different hardness, but may comprise a single silicone layer or multiple layers of silicone beyond just the two described herein.

The liner is not limited to being formed at least in part from silicone. Other suitable polymeric materials for use in liners may used, as explained in greater detail in U.S. Pat. Nos. 6,706,364 and 6,964,688, both of which are incorporated herein by reference.

The embodiments of the liner described herein are not limited to being formed with corresponding matrix materials. Instead, they may be made without any matrix materials, and solely with molded polymeric materials. Additionally, a liner may be provided with at least one covering or segments thereof which cover the outer portion of the polymeric portions of the liner but do not necessarily serve as a reinforcing material.

A liner having a seal or plurality of seals is advantageous in that it does not strangle a residual limb on trans-tibial users since the plurality of seals more evenly distribute traction than a single seal system. It follows that by providing multiple seals, the seal does not create localized pressure peaks on the residual limb. The strangling of residual limbs may occur at bony or sensitive areas of the residual limb.

Figure 4:
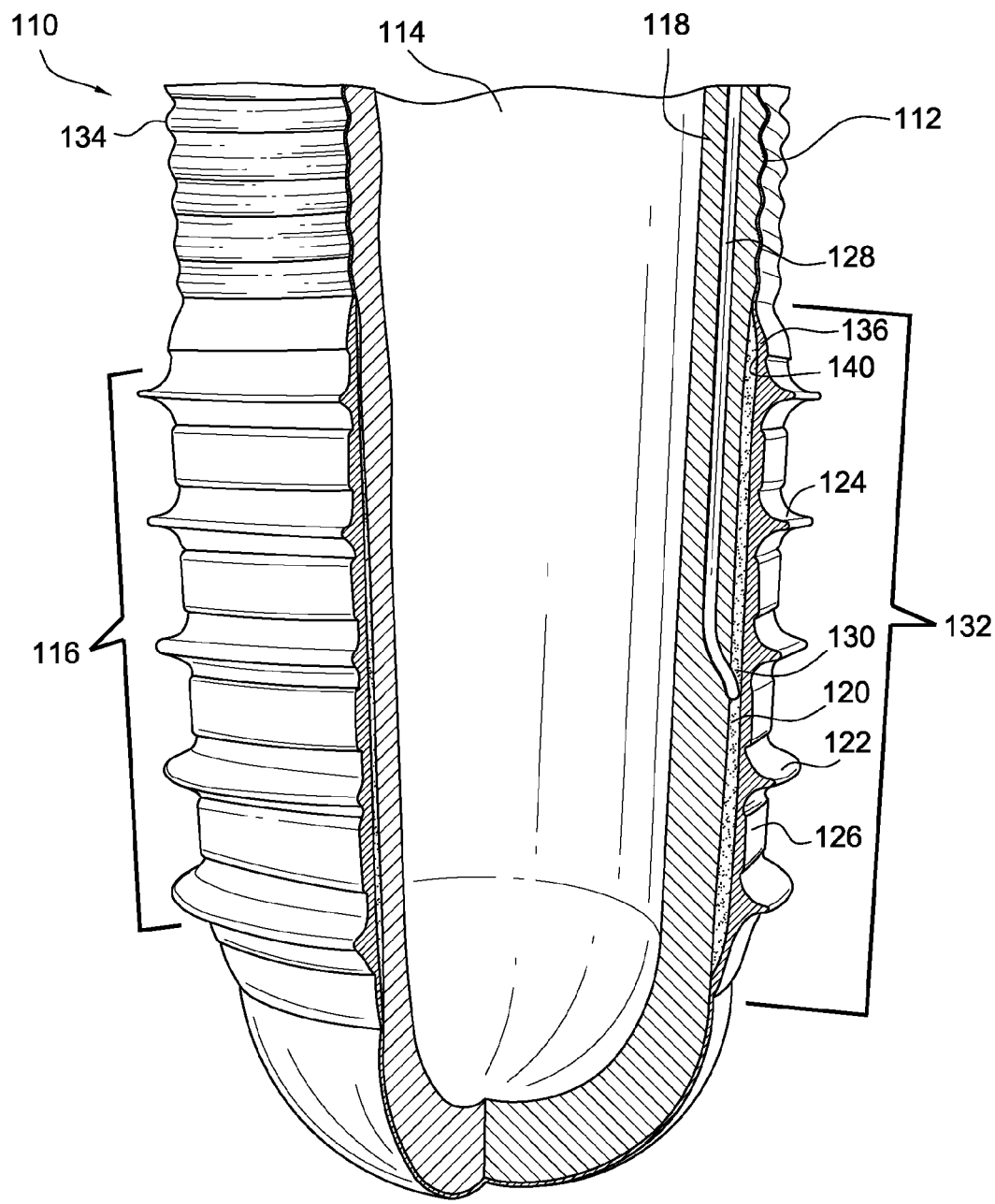
FIG. 4 is an elevational view according to an embodiment of a suspension liner having a distensible seal in a non-distended configuration.

Turning to FIG. 4, an embodiment of the invention includes a liner 110 with a seal element 116 having a volume control pad 120. As with the prior art embodiment of FIGS. 1-3, the liner 110 is adapted to provide an interface between a residual limb and a prosthetic socket. The liner 110 is depicted in truncated form, primarily showing a distal end portion. The portions of the liner 110 outside of the distal end portion may take the form of the liner according to FIGS. 1-3, or other liners known in the art.

The liner 110 includes an elongate, generally conical body portion 118 formed from at least one material segment, such as from an elastomeric material. The liner defines proximal and distal end portions, as known from prior art liners.

The liner defines a resilient seal element 122, forming part of a plurality of seal elements 116. The seal element 122 radially protrudes from the body portion 118, and extends about at least a portion of the periphery of the body portion 118. Preferably, the seal element 122 is annular in form and extends about the peripheral circumference of the liner body portion 118. However, the seal element may be provided in segments about the periphery of the body portion.

Each seal element 122 defines a peak or outwardly extending portion 124 and a clearance 126 formed between each seal element 122. A continuous textile material layer 112 covers may cover portions of the body portion above and below the seal elements 116. Alternatively, the textile material may extend across the entirety of the periphery of the body portion or a portion across the area in correspondence with the seal element, such that the seal element is formed or adhered over the textile material.

The body portion may have a substantially same thickness in areas adjacent to the seal element. Likewise, the thickness of the body portion may have a thickness that is substantially the same both in correspondence with the seal element and in areas above and below or adjacent to the seal element, notwithstanding a passageway that may be located within the thickness of the body portion. Alternatively, the thickness of the body portion may be reduced in an area in correspondence with the seal element.

Figure 5:
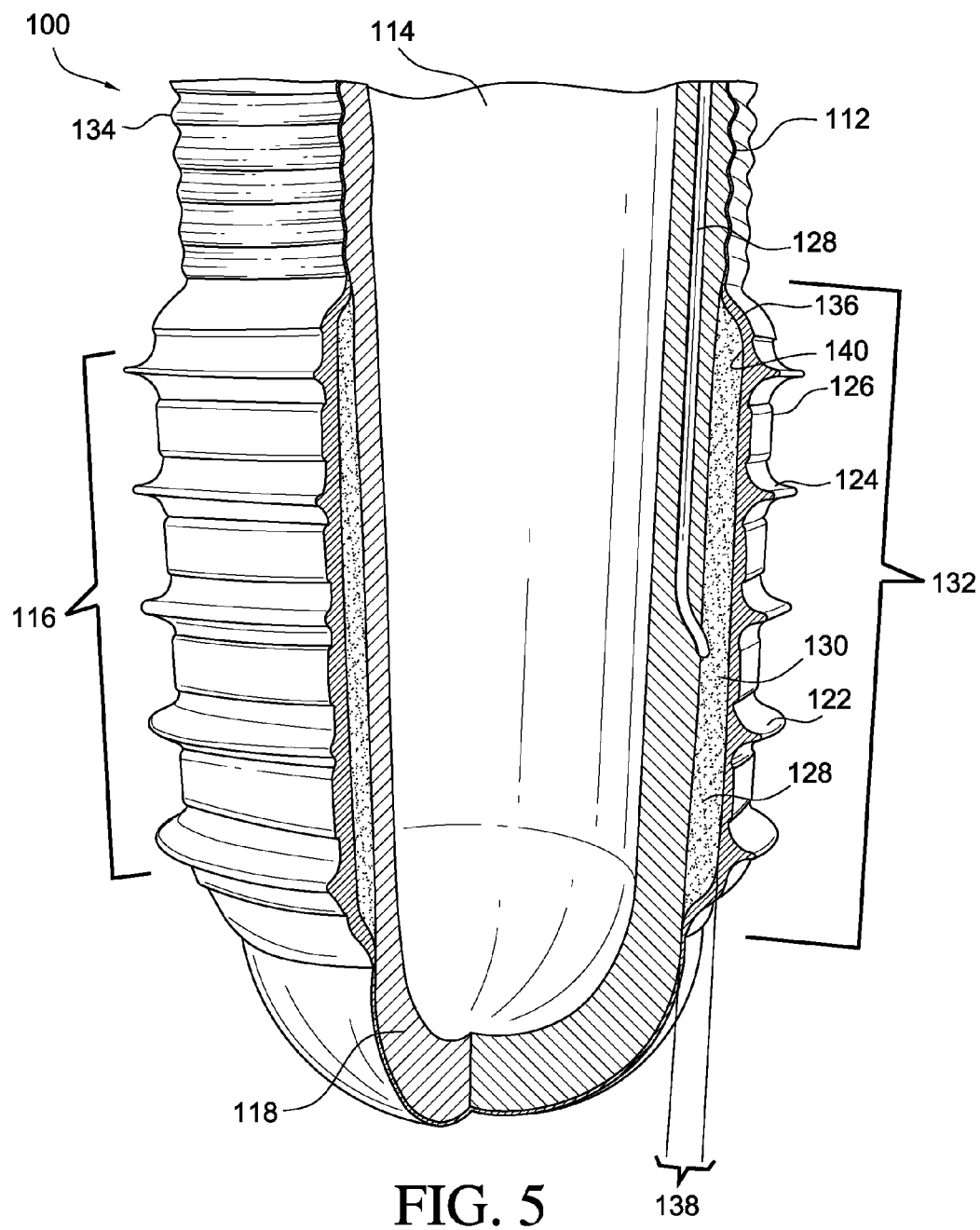
FIG. 5 is an elevational view according to the embodiment of FIG. 4 in a distended configuration.

According to the embodiment of FIGS. 4 and 5, the seal elements 116 are formed by an outer seal piece 136 fixedly secured to the peripheral circumference of the body portion 114. The outer seal piece 136 is formed from an elastomeric material to allow for distension due to expansion of the volume control pad. The outer seal piece 136 preferably forms a recess 140 between individual seal elements 122 and the volume control pad 120 is configured and dimensioned to fit within the recess 140.

As noted above, the seal element is not limited to the construction depicted in FIGS. 4 and 5, but any number of seal elements may be used in combination with the volume control pad. In accordance with this disclosure, the geometry of the seal element is of less importance, but what is important is the combination of the seal element with a volume control pad.

Despite the depiction of seal elements, the liner may be provided without the seal element, and instead the volume control pad is provided between the body portion and the outer layer, such as the textile layer. A frictional coating, in the form of a seal element, may be provided on the outer layer in correspondence with the volume control pad to provide a frictional fit between the liner and the prosthetic socket.

The volume control pad 120 is located between the body portion 118 and the seal elements 116. The volume control pad 120 is arranged to distend from the body portion 118 and urge the seal elements 116 outwardly from the body portion 118. While the seal elements 116 annularly extend about the body portion 118, the volume control pad 120 annularly extends between the body portion 118 and the seal element 116 in correspondence with the seal elements 116.

Alternatively, the volume control pad may be located along an outer textile layer covering the body portion, such that the volume control pad is located between the outer layer and the seal element. Moreover, in combination with any of the embodiments, the volume control need only be in part correspondence to seal element, and the disclosure is not limited to the volume control pad being in entire correspondence with the seal element.

According to the embodiment of FIGS. 4 and 5, a passageway 128 is defined within the thickness of the body portion 118 and is in correspondence with the volume control pad 120. The passageway may be formed as a tube for the introduction of an appropriate medium into the volume control pad, and for withdrawal of the medium from the volume control pad. The passageway may be formed within the thickness of the liner body or alternatively may be a separate tube integrated within the thickness of the liner body.

In a preferred embodiment, the passageway is a silicone tube cast into the thickness of the liner body. The passageway extends between the volume control pad and exits at the proximal end of the liner. A pump can be removably connected to an outlet of the passageway so as to allow for inflation of the volume control pad. Alternatively, the passageway may exit from the suspension sleeve at a location closer to the volume control pad, and may also be arranged to extend through the wall thickness of the socket so as to secure to a pump.

The volume control pad 120 may be formed as a core surrounded by a flexible shell. The core may be filled with air, a fluid, gel or other appropriate medium 130 that allows for expansion of the flexible shell to distend the seal elements 116 outwardly away from the liner body 118. Exemplary volume control pads include those described in U.S. Pat. Nos. 6,936,073 and 6,923,834, incorporated herein by reference.

The volume control pad may be formed as a single expandable pad, or alternatively may comprise a plurality of different individually expandable pads. The volume control pad may likewise correspond to different sections of the seal element or elements, so that one pad may distend more or be capable of having a greater volume expanded than another pad corresponding to a different section of the seal element or elements.

FIG. 4 represents the volume control pad having little or no volume ("non-expanded" condition) and FIG. 5 represents the volume control pad as having the volume of the volume control pad increased ("expanded" condition). From these different conditions of the volume control pad, FIG. 5 shows how a section 132 of the liner 100 corresponding to the volume control pad and the seal elements distends outwardly from the liner body a distance 138 in the expanded condition relative to the non-expanded condition of FIG. 4.

The volume control pad allows for improving the interface of the seal elements with the wall of the intended socket to be worn by the amputee. By adjusting the volume of the volume control pad, the interface of the liner can be adjusted according to different conditions of the residual limb upon which the liner is worn.

The liner may include a plurality of peripheral profiles 134 as described in U.S. Pat. Nos. 7,169,189 and 7,118,602, each being incorporated herein by reference.

The liner allows for some error in making the socket and accounts for volume fluctuations of the residual limb. The volume control pad allows for the seal element or elements to be urged outwardly toward a wall of a hard socket. The volume control pad may be fed by the passageway through a silicone tube cast in the thickness of the liner body wall, by extending from the volume control pad to the proximal end of the liner or other appropriate location along the liner body length. A pump may be detachably mounted to the passageway. From this system, an amputee can adjust the liner itself rather than have the socket modified by a prosthetist.

It will be understood that the aforementioned embodiments of the present invention are not limited to the described combination of the liner body portion, seal element and hard socket. Instead, the features of one of the preferred embodiments of the present invention may readily be combined with those of another or other embodiments of the present invention without departing from the scope of the present invention.

It will be readily understood that the described embodiments of the invention are exemplary only and various other features and details could be incorporated in the system described herein without departing from the spirit and scope of the invention as defined in the appended claims.

The invention claimed is:

1. A suspension liner adapted to provide an interface between a residual limb and a prosthetic socket, the suspension liner comprising:
    an elongate, generally conical body portion including proximal and distal end areas; and
    at least one resilient seal element protruding radially from and extending along a segment short of an entire longitudinal length of the body portion at the distal end area of the body portion, the seal element formed from an elastomeric material and fixedly secured to a periphery of the body portion along said segment;
    a volume control pad located between the body portion and at least a portion of the seal element, the volume control pad arranged to be pressurized so as to distend from the body portion and urge the seal element outwardly from the body portion; and
    a passageway having a first end in fluid communication with the volume control pad and a second end forming an outlet from the body portion;
    wherein the volume control pad is arranged in correspondence with and in the proximity of the seal element;
    wherein the at least one seal element is formed by an outer seal piece fixedly secured to the peripheral circumference of the body portion, the outer seal piece forming a recess into which the volume control pad is configured and dimensioned to fit within.

2. The suspension liner according to claim 1, wherein the seal element annularly extends about the body portion, the volume control pad annularly extending between the body portion and the seal element.

3. The suspension liner according to claim 1, wherein the body portion is formed from an elastomeric polymer.

4. The suspension liner according to claim 1, wherein the passageway is defined within the thickness of the body portion.

5. The suspension liner according to claim 1, wherein a textile material covers portions of the body portion at least at locations above and below end portions of the seal element.

6. The suspension liner according to claim 1, wherein a thickness of the body portion is substantially the same at portions adjacent the seal element.

7. The suspension liner according to claim 1, wherein the seal element defines an outwardly extending portion defining at least one peak and a portion without said peak.

8. The suspension liner according to claim 1, wherein proximal and distal ends of the outer seal piece secure to the body portion with the recess formed between the proximal and distal ends.

9. The suspension liner according to claim 1, wherein the body portion consists of a single layer and has a substantially same thickness in areas adjacent to the at least one seal element and in areas above and below the at least one seal element.

10. A suspension liner adapted to provide an interface between a residual limb and a prosthetic socket, the suspension liner comprising:
- an elongate, generally conical body portion formed from at least one material layer, and including proximal and distal end areas;
- at least one resilient seal element protruding radially from and extending along a segment short of an entire longitudinal length of the body portion at the distal end area of the body portion, the seal element formed from an elastomeric material and fixedly secured to a periphery of the body portion along said segment;
- a volume control pad located between the body portion and the seal element, the volume control pad arranged to be pressurized so as to distend from the body portion and urge the seal element outwardly from the body portion; and
- a passageway defined within the thickness of the body portion, the passageway having a first end in fluid communication with the volume control pad and a second end forming an outlet from the body portion;
- wherein the volume control pad is arranged in correspondence with and in the proximity of the seal element;
- wherein the at least one seal element is formed by an outer seal piece fixedly secured to the peripheral circumference of the body portion, the outer seal piece forming a recess into which the volume control pad is configured and dimensioned to fit within.

11. The suspension liner according to claim 10, wherein the at least one material layer includes an elastomeric layer having a thickness into which the passageway extends.

12. The suspension liner according to claim 10, wherein the at least one material layer includes an elastomeric layer, the entirety of the passageway is formed within the elastomeric layer.

13. The suspension liner according to claim 10, wherein the seal element defines an outwardly extending portion defining at least one peak and a portion without said peak.

14. The suspension liner according to claim 10, wherein proximal and distal ends of the outer seal piece secure to the body portion with the recess formed between the proximal and distal ends.

* * * * *